(12) United States Patent
Single

(10) Patent No.: US 7,751,897 B2
(45) Date of Patent: Jul. 6, 2010

(54) TEMPERATURE REGULATED IMPLANT

(75) Inventor: Peter Single, Lane Cove (AU)

(73) Assignee: Cochlear Limited, Lane Cove, NSW (AU)

( * ) Notice: Subject to any disclaimer, the term of this patent is extended or adjusted under 35 U.S.C. 154(b) by 207 days.

(21) Appl. No.: 10/910,589

(22) Filed: Aug. 4, 2004

(65) Prior Publication Data

US 2005/0033382 A1 Feb. 10, 2005

(30) Foreign Application Priority Data

Aug. 4, 2003 (AU) .............................. 2003904086

(51) Int. Cl.
*A61N 1/00* (2006.01)
(52) U.S. Cl. .......................................... 607/57; 607/63
(58) Field of Classification Search ............. 607/55–57, 607/63
See application file for complete search history.

(56) References Cited

U.S. PATENT DOCUMENTS

| | | | |
|---|---|---|---|
| 4,532,930 A | 8/1985 | Crosby et al. | |
| 5,046,242 A | 9/1991 | Kuzma | |
| 5,279,292 A | 1/1994 | Baumann et al. | |
| 5,411,467 A | 5/1995 | Hortmann et al. | |
| 5,601,617 A * | 2/1997 | Loeb et al. | 607/56 |
| 5,645,585 A | 7/1997 | Kuzma | |
| 5,814,095 A | 9/1998 | Müller et al. | |
| 5,935,166 A | 8/1999 | Kennedy | |
| 5,984,953 A * | 11/1999 | Sabin et al. | 607/114 |
| 6,067,474 A | 5/2000 | Schulman et al. | |
| 6,272,382 B1 | 8/2001 | Faltys et al. | |
| 6,308,101 B1 * | 10/2001 | Faltys et al. | 607/57 |
| 6,358,281 B1 * | 3/2002 | Berrang et al. | 623/10 |
| 6,516,228 B1 | 2/2003 | Berrang et al. | |
| 6,531,847 B1 * | 3/2003 | Tsukamoto et al. | 320/135 |
| 6,553,263 B1 | 4/2003 | Meadows et al. | |
| 6,586,912 B1 * | 7/2003 | Tsukamoto et al. | 320/150 |
| 6,636,768 B1 * | 10/2003 | Harrison | 607/57 |
| 6,648,914 B2 * | 11/2003 | Berrang et al. | 623/10 |
| 6,736,770 B2 * | 5/2004 | Leysieffer et al. | 600/25 |
| 6,855,422 B2 * | 2/2005 | Magill et al. | 428/373 |
| 6,891,353 B2 * | 5/2005 | Tsukamoto et al. | 320/136 |
| 6,894,456 B2 * | 5/2005 | Tsukamoto et al. | 320/107 |
| 6,922,591 B2 * | 7/2005 | Single | 607/57 |

FOREIGN PATENT DOCUMENTS

AU 26017/99 A1 3/2000

(Continued)

OTHER PUBLICATIONS

International Search Report for PCT/AU01/00769, dated Jul. 19, 2001.

(Continued)

*Primary Examiner*—Scott M Getzow
(74) *Attorney, Agent, or Firm*—Connolly Bove Lodge & Hutz LLP

(57) ABSTRACT

One disclosed embodiment of the present invention is a medical device having an electronic assembly and battery contained within a housing. Sealed in the housing is a heat absorption medium for regulating the temperature of the medial device, wherein said heat absorption medium undergoes a state change at a state change temperature of 36° Celsius or greater.

45 Claims, 3 Drawing Sheets

FOREIGN PATENT DOCUMENTS

| | | |
|---|---|---|
| AU | 26969/99 A | 3/2000 |
| AU | 199926017 B2 | 3/2000 |
| WO | WO-94/17645 A1 | 8/1994 |
| WO | WO-97/44987 A1 | 11/1997 |
| WO | WO 99/08108 | 2/1999 |
| WO | WO 99/41067 | 8/1999 |
| WO | WO-01/39830 A2 | 6/2001 |
| WO | WO 01/74278 A2 | 10/2001 |

OTHER PUBLICATIONS

International Preliminary Examination Report for PCT/AU01/00769 dated Sep. 27, 2002.
Written Opinion for PCT/AU01/00769, dated Feb. 18, 2002.
Written Opinion for PCT/AU01/00769 dated Feb. 18, 2002.

* cited by examiner

TEMPERATURE REGULATED IMPLANT

CROSS-REFERENCE TO RELATED APPLICATIONS

This application claims priority from Australian Provisional Patent Application No. 2003904086, entitled "Implant Battery Short Circuit Protection," filed Aug. 4, 2003, which is hereby incorporated by reference herein in its entirety.

This application is related to U.S. Patent Application Publication No. 2003/0171787, which is hereby incorporated by reference herein in its entirety.

BACKGROUND

1. Field of the Invention

The present invention relates generally to implantable medical devices and, more particularly, to a temperature regulated implantable medical device.

2. Related Art

The use of implantable medical devices to provide therapy to individuals for various medical conditions has become more widespread as the advantages and benefits such devices provide become more widely appreciated and accepted throughout the population. In particular, devices such as hearing aids, implantable pacemakers, defibrillators, functional electrical stimulation devices such as Cochlear™ prostheses, organ assist or replacement devices, and other partially- or completely-implanted medical devices, have been successful in performing life saving and/or lifestyle enhancement functions for a number of years.

Many such implantable medical devices often include one or more sensors, processors, controllers or other functional mechanical, electrical or electronic components that are permanently or temporarily implanted in a patient. Many of these devices receive power and/or data from external components that are part of, or operate in conjunction with, the implanted medical device. In particular, many such implantable devices include a power source integrated into the device. Some larger systems include more than one implantable device of which one is a power source which provides power to another implantable device. Such power sources are typically rechargeable batteries although other types of power sources have be implemented as well.

One such type of medical device is a Cochlear™ implant system. Cochlear™ implant systems provide the benefit of hearing to individuals suffering from severe to profound hearing loss. Hearing loss in such individuals is due to the absence or destruction of the hair cells in the cochlea which transduce acoustic signals into nerve impulses. Cochlear™ implants essentially simulate the cochlear hair cells by directly delivering electrical stimulation to the auditory nerve fibers. This causes the brain to perceive a hearing sensation resembling the natural hearing sensation normally delivered to the auditory nerve.

Conventional Cochlear™ implant systems have generally included an external assembly directly or indirectly attached to the body of the patient (sometimes referred to herein as the recipient), and an internal assembly which is implanted in the patient. More recently, Cochlear™ implant systems have been designed such that all of the systems' components are implanted subcutaneously; that is there is no external assembly. Because such Cochlear™ implant systems are entirely implantable, they are commonly referred to as a "totally" implantable Cochlear™ implant. This results in a more versatile system providing the recipient with greater freedom and ability to use the implant in what would previously have been regarded as adverse environments, e.g. wet environments. Such a Cochlear™ implant system is described in greater detail in U.S. Patent Application Publication No. 2003/0171787, which is hereby incorporated by reference herein. However, unlike earlier Cochlear™ implant systems, the totally implantable system is powered by a rechargeable battery that receives power transcutaneously via an implanted receiver coil.

In a totally implantable Cochlear™ implant device as well as other implantable medical devices which include a power source, there is a risk that a malfunction in the components that utilize or regulate the power consumption of the implantable device, or a malfunction in the power source itself, may cause excessive heat to be released. For example, if a malfunction causes an implantable battery to short circuit, the battery may rapidly discharge causing a rapid rise in temperature. Such an increase in temperature can damage the battery and the implanted components. This may cause the medical device to cease operating which, if the device is life sustaining, can be catastrophic. Alternatively, component failure due to overheating may necessitate replacement of the implantable component, which requires surgery. Furthermore, should the heat be conducted to the housing of the implanted device, such heat can be conducted to the surrounding tissue causing discomfort and possibly necrosis.

SUMMARY

According to one aspect of the present invention, an implantable medical device is disclosed. The medical device comprises: a biocompatible housing; a power source mounted in said housing; and a heat absorption medium occupying interstices in said housing and thermally coupled to at least said power supply, wherein said heat absorption medium absorbs heat as it undergoes a state change at a state change temperature which prevents said housing from substantially exceeding a device temperature threshold.

According to another aspect of the present invention, an implantable medical device is disclosed. The medical device comprises: a housing; electronic components contained within said housing; and a heat absorption medium sealed within said housing for regulating the temperature of said device, wherein said heat absorption medium undergoes a state change at a state change temperature of approximately 36° Celsius or greater.

According to a further aspect of the present invention, an implantable hearing prosthesis is disclosed. The hearing prosthesis comprises: a hermetically sealed, biocompatible housing having mounted therein an electronic assembly and a power source; and a heat absorption medium disposed within said housing so as to be thermally coupled to at least said power supply, wherein said heat absorption medium absorbs heat as it undergoes a state change at a state change temperature which prevents said housing from substantially exceeding a device temperature threshold.

DETAILED DESCRIPTION

Embodiments of the present invention are directed to an implantable medical device containing a power source and a heat absorption medium in a biocompatible housing. The heat absorption medium occupies interstices inside the housing so as to be thermally coupled to the power source, and preferably in direct contact with the power source. The heat absorption medium is configured to undergo a state change (for example, solid to liquid, liquid to gas, solid to gas, etc.) when its temperature rises above a predetermined threshold value. Advantageously, should a malfunction occur in the implantable device that causes the energy stored in the power source to be converted to heat, the heat is utilized to change the state of the heat absorption medium thereby preventing the heat from being transferred via conduction or convection from the power source to electronic components (if included in the device), the device housing, and/or the surrounding tissue or bone. The temperature of the implantable device, therefore, is maintained at a safe temperature despite such a malfunction, preventing damage to the device and patient.

The implantable medical device implementing an embodiment of the present invention can be any implantable medical device now or later developed which includes a power source. Such an implantable medical device can be either partially or totally implanted in an individual, and such implantation may be temporary or permanent. Examples of implantable medical devices include stimulating devices such as Cochlear™ implants, pacemakers, defibrillators, gastrointestinal stimulators and the like; monitoring systems, organ assist or replacement devices, devices that dispense synthetic or natural agents, etc., as well as implantable devices that include a power supply that supplies power to another implantable medical device that consumes power to perform some therapeutic function.

Figure 1:
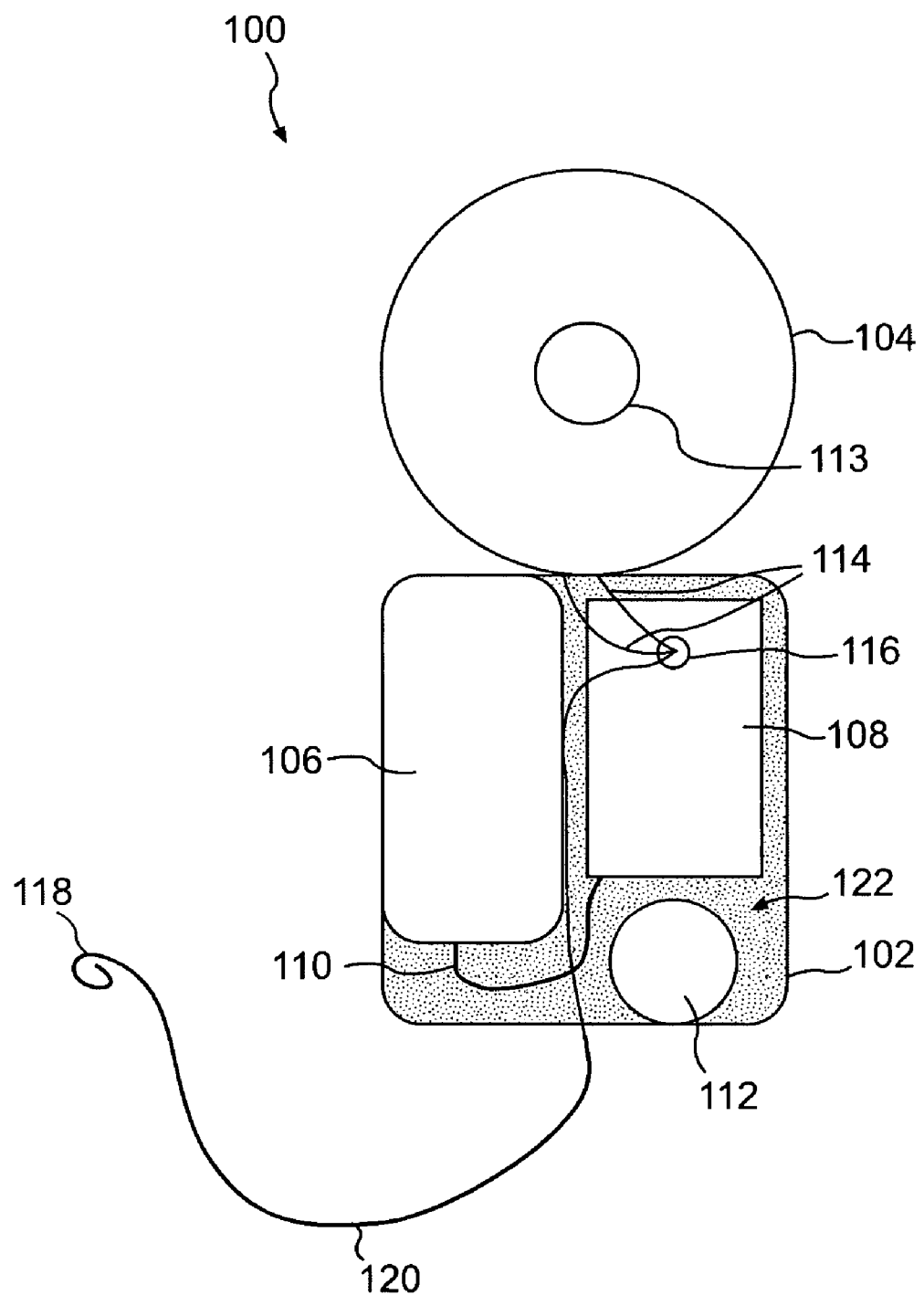
FIG. 1 is an exposed view of a portion of a totally implantable Cochlear™ implant system in accordance with one embodiment of the present invention.

Embodiments of the present invention are described below in connection with one embodiment of an exemplary implantable medical device, a totally implantable Cochlear™ prosthesis (also referred to as a Cochlear™ implant system, Cochlear™ prosthetic device and the like). FIG. 1 illustrates one exemplary embodiment of such a totally implantable Cochlear™ prosthesis, referred to as a Cochlear™ implant device 100. Cochlear™ implant device 100 provides direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, an alternative embodiment of Cochlear™ implant system 100 provides stimulation of the cochlear nucleus in the brainstem.

Generally, implantable device 100 comprises a housing 102 and a receiver coil 104. Receiver coil 104 is mounted externally of housing 102 and is connected to housing 102 via external leads 114 and a feedthrough 116. In one embodiment, receiver coil 104 may be a three-turn electrically insulated platinum or gold wire antenna coil. In the embodiment shown in FIG. 1, receiver coil 104 is mounted in a flexible silicone molding that is secured to the exterior of housing 102.

Receiver coil 104 has a magnet 113 centrally located in coil 104. The magnet assists in the alignment and attachment of an external coil unit (not shown). Such an external coil may be used for recharging an internal battery when the power source mounted in housing 102 is a rechargeable power source. Communication between receiver coil 104 and the external coil may also be used for effecting bi-directional data transfer between the implant and external devices, where required.

Housing 102 contains a power source 106, an electronic assembly 108 including various electronic components of the implant (not shown for convenience). The electronic components may include a speech processor, a receiver/stimulator and other well-known functional components of the Cochlear™ implant device. A microphone 112 is mounted in housing 102 for receiving external sound signals for transmission to electronic assembly 108 for processing. Microphone 112 may be any microphone suitable for use in implant 100. For example, microphone 112 may be a single cavity microphone, a directional, dual cavity microphone, etc.

Stimulation signals generated by the speech processor of implant 100 are fed to an electrode array 118. Electrode array 118 is also connected to electronic assembly 108 via a lead 120 and feedthrough 116. As used herein, when the term electronic components is used to refer to the components contained in housing 102, such term refers to all components other than power source 106, including microphone 112, unless otherwise noted or obvious from the context in which the term is used. A detailed description of various embodiments of Cochlear™ implant system 100 is provided in U.S. Patent Application Publication No. 2003/0171787 which is hereby incorporated by reference herein.

Housing 102 is preferably hermetically sealed. In one embodiment, the housing of the implant of the present invention is made of a biocompatible material such as plastic, rubber, ceramic, etc. In one embodiment, the housing is formed of hermetically sealed titanium. Prior to implantation, the housing may be coated with a layer of silicone or parylene or other protective coatings as a further protective measure for the implant.

Power source 106 is connected to electronic assembly 108 by an internal lead 110. Implantable power source 106 stores energy which is utilized to power electronic, mechanical, electro-mechanical, communication and/or other components of implantable medical device 100 which require power to function. The present invention can be implemented in connection with any such power source now or later developed including, but not limited to, rechargeable and non-rechargeable batteries, radioactive isotopes, capacitor banks, etc., or any combination thereof. In this exemplary embodiment, power source 106 is a rechargeable lithium-ion battery. It should be appreciated that in alternative embodiments in which multiple power sources are utilized, power source 106 can further include circuitry to select which of such multiple power sources are to be utilized at any given time to provide power to device 100, and which, for example, are to be charged. For example, in some embodiments, power source 106 comprises two or more batteries with circuitry that permits one battery to be recharged while the other battery concurrently supplies power to the electronic components of device 100.

Figure 2:
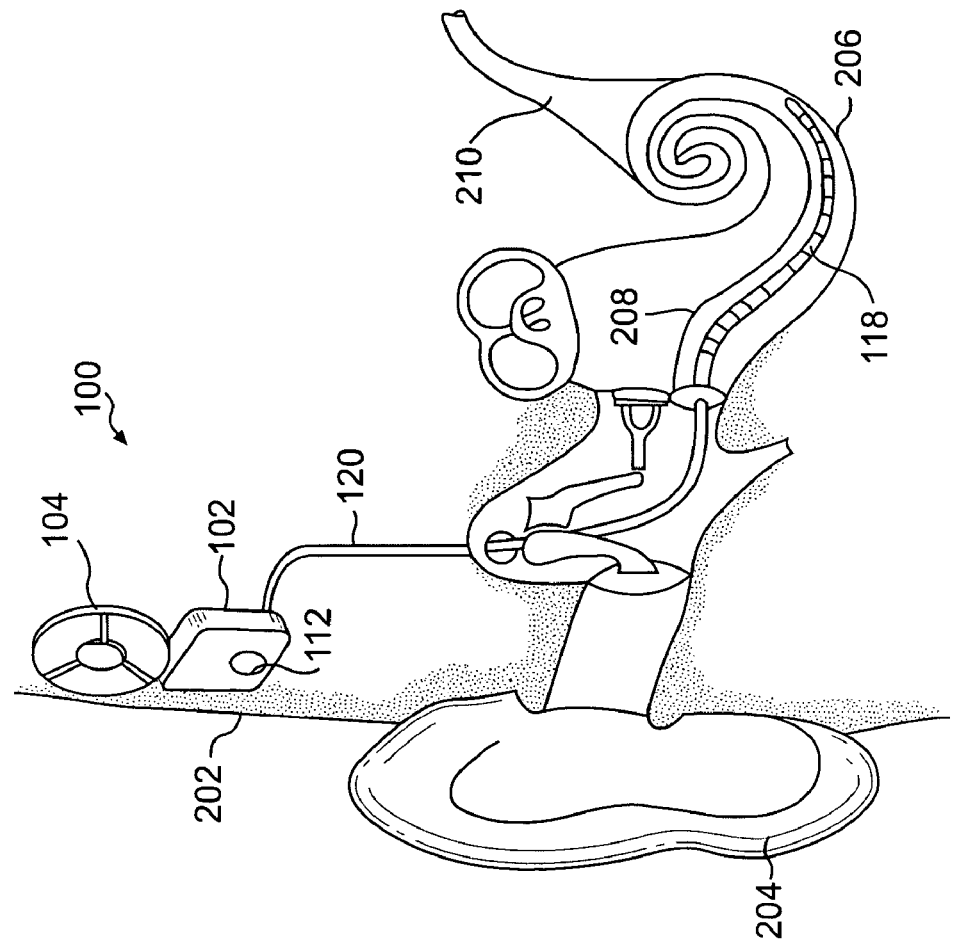
FIG. 2 is a simplified representation of the implant of FIG. 1 implanted in the skull of an individual.

FIG. 2 is a simplified perspective view of one embodiment of a totally implantable Cochlear™ implant system 100 shown implanted in a recipient. Implant 100 is a totally self-contained unit implanted in an excavated region of a temporal bone of an individual's skull 202 adjacent to an ear 204 of the individual. As shown in FIG. 2, implant 100, when implanted in an individual's skull 202, has no external or externally accessible components. Electrode array 118 is mounted in the cochlea 206 of the recipient. When stimulation signals are received by electrode array 118 these signals are transmitted to the basilar membrane 208 to stimulate the recipient's auditory nerve 210.

Referring again to FIG. 1, in accordance with the teachings of the present invention, heat absorption medium 122 is included in housing 102. As noted, heat absorption medium 122 is thermally coupled to power source 106. Preferably, heat absorption medium 122 is in direct contact with power source 106 and, more preferably, heat absorption medium 122 is preferably in direct contact with a substantial portion of available surface area of power source 106 to maximize the conduction of heat from power source 106 to heat absorption medium 122.

In the illustration depicted in FIG. 1, heat absorption medium 122 also covers power source 116 and, perhaps, the other components mounted in housing 102. However, the portion of heat absorption medium 122 which covers such components is not shown for ease of illustration. In the embodiment shown in FIG. 1, heat absorption medium 122 also fills the interstices created between housing 102 and the various elements it contains, as well as between various components of housing 102 including the spaces between power source 106 and electronic assembly 108 and microphone 122. Preferably, the heat absorption medium 122 included in housing 102 is contiguous to enable the entire mass of material to directly absorb heat generated by power supply 106.

In use, as shown in FIG. 2, implant 100 operates at body temperature of approximately 37° Celsius. Normal bodily processes maintain implant 100 at that temperature. However, there is a risk that a malfunction in components of power source 106 or electronic assembly 108 that utilize or regulate the power consumption of the implantable components 104, 106 and 122, or a malfunction in power source 106, may cause the current drawn from power source 106 may become unregulated, causing power source 106 to convert its stored energy to excessive heat rather than regulated power. As noted, such an increase in temperature may be too high for normal heat dissipation and bodily processes to maintain implant 100 at or below approximately 37° Celsius or some other maximum temperature threshold above which adverse effects are experienced by either the implantable device and/ or the recipient. Such an occurrence may damage power source 106, electronic assembly 108, microphone 122 and/or receiver coil 104, or may cause discomfort and possibly necrosis of surrounding tissue.

Heat absorption medium 122 is constructed and arranged to absorb heat that may be released by power source 106 or any other component contained in housing 102. As noted, heat absorption medium 122 absorbs such heat by changing state. Such a state change can be any change in the state that allows a material to absorb heat without significantly raising the temperature of that material. For example, a state change may be a phase change such as from solid to liquid, liquid to gas, solid to gas, etc. A state change may also refer to a material transitioning from one form to another: crystalline to amorphous, from non-viscous to viscous, etc. As one of ordinary skill in the art would appreciate, a variety of terms are used to refer to the heat absorbed by a unit mass of heat absorption medium 122 when changing state, such as "heat of fusion" (when changing from a solid to a liquid), "heat of vaporization" (when changing from a liquid to a vapor), etc. The term "heat of state transition" will be used herein to generally refer to such heat absorption regardless of the type state change.

Preferably, the quantity of heat absorption medium 122 which is included in housing 102 is sufficient to absorb at least a portion of the heat generated by power source 106 to prevent housing 102 to exceed the noted temperature threshold for implantable device 100. Such a quantity is based on one or more of a variety of factors including the anticipated heat that may be generated by power source 106, the available space inside housing 102, the capability of expanding the size of housing 102 and, hence, the quantity of heat absorption medium 122 that may be included in housing 102, the heat that is absorbed by heat absorption medium 122 when it transitions state (i.e., its heat of state transition), the temperature that housing 102 and electronics contained in the housing can attain; i.e., its threshold temperature, the surface area over which heat absorption medium 122 contacts power source 106, the capability of intervening elements between power source 106 and heat absorption medium 122 to conduct heat, and other factors.

For example, the maximum heat that may be generated by power source 106 is determined by the maximum quantity of energy that the power source can store. However, in the case in which a malfunction occurs when power source 106 is storing its maximum energy, some of the heat generated by power source 106 may be absorbed by housing 102, electronic assembly 108, and the patient's body. In such embodiments, the maximum heat that may need to be absorbed by heat absorption medium 122 may be less than the maximum heat that can be generated by power source 106.

As noted, implant 100 operates at body temperature of approximately 37° Celsius. In one embodiment, heat absorption medium 122 is a solid with a melting point in the range of above or only slightly below 37° Celsius. In one embodiment, heat absorption medium 122 has a melting point in the range of approximately 36° to 43° Celsius. In a further embodiment, head absorption medium 122 has a melting point in the range of about 39 to 41° Celsius. As one of ordinary skill in the art would appreciate, the temperature at which heat absorption medium 122 changes state is selected based on one or more of the above and, perhaps, other factors.

Figure 3:
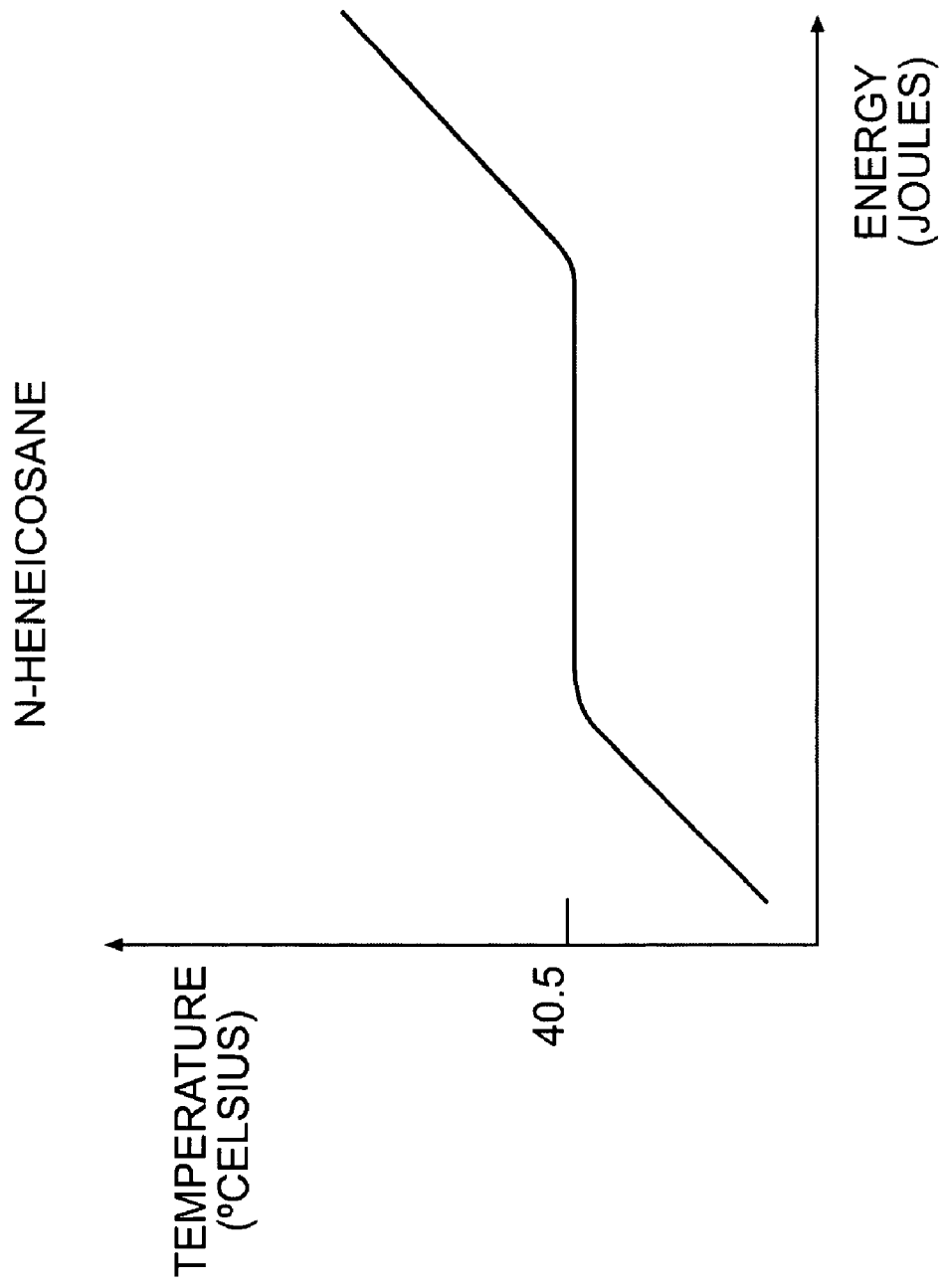
FIG. 3 is a simplified graph of temperature vs. energy for n-heneicosane, a heat absorption medium that may be used in accordance with one embodiment of the present invention.

In one embodiment, heat absorption medium 122 may be a saturated hydrocarbon of the methane series. In one embodiment of the present invention, the heat absorption medium is n-heneicosane, which has a waxy consistency as a solid and which has a melting point of about 40.5° Celsius. FIG. 3 is a simplified graph of temperature vs. energy for n-heneicosane that shows how n-heneicosane is able to absorb a significant amount of heat energy at n-heneicosane's melting point of 40.5° Celsius without the temperature of n-heneicosane rising.

As one of ordinary skill in the art would find apparent, other materials may be used individually or in combination to provide heat absorption mediums 122 of the present invention. In one embodiment, the heat absorption medium may be an aliphatic hydrocarbon, either branched or unbranched, that has a melting point of approximately greater than approximately 34° Celsius and, preferably of approximately 40° Celsius. It should be appreciated that in alternative embodiment, heat absorption medium 122 may be a mixture of materials. For example, a first material with a higher state transition temperature may be doped with an amount of a second material to depress the state transition temperature of the resulting mixture. It should also be appreciated that in alternative embodiments heat absorption medium 122 may comprise other materials that absorb heat when changing state. Preferably, heat absorption medium 122 is biocompatible to insure patient safety should the heat absorption medium escape from housing 102.

Referring again to FIG. 1, the illustrative embodiment of housing 102 has a volume of approximately 5 ccs. In such a housing, approximately 2-3 cc's of a heat absorption medium 122, such as n-heneicosane, may be contained in the housing. When n-heneicosane is the absorption medium, n-heneicosane may be potted, melted or poured on the inside of housing 102 over and around power source 106 and, preferably, electronic assembly 108 and microphone 112. It should be appreciated that any application technique suitable for the application and consistency of heat absorption medium 122 may be utilized. As noted, it is preferably that the maximum surface area of power source 106 be covered with heat absorption medium 122 to facilitate heat transfer between the two.

N-heneicosane has a heat of fusion of 213 Joules/gram. So about 3 grams of n-heneicosane can absorb 639 Joules. One embodiment of power source 106 in Cochlear™ implant device 100 comprises a rechargeable lithium-ion battery which can store approximately 470 Joules of energy. As a result, when using about 3 grams n-heneicosane as heat absorption medium 122 in housing 102, such a power source 106 may dump the battery's entire charge without the temperature of housing 102 rising above 40.5° Celsius. Also, because housing 102 itself may be a heat conductor, some of the heat energy within the housing may, as noted, be partially dissipated through the housing and conducted away from the housing by normal bodily processes. In one embodiment, an implant of the present invention includes enough heat absorption medium 122 having a sufficiently large heat of fusion to allow the heat absorption medium in the implant to absorb at least 470 Joules of energy before heat absorption medium 122 rises in temperature above its state transition temperature, which would permit the temperature of housing 102 to rise above its threshold temperature.

In operation, when the temperature inside housing 102 reaches a threshold temperature, heat absorption medium 122 undergoes a state change, such as melting, during which heat absorption medium 122 absorbs heat while maintaining the temperature of the interior of housing 102 at its threshold temperature. Once power source 106, has totally discharged, housing 102 may remain at the elevated temperature for a period of time while normal bodily processes continue to conduct heat away from the housing. As this occurs, heat absorption medium 122 re-solidifies by expelling its heat.

In addition to having the above thermal properties, heat absorption medium 122 preferably is electrically non-conductive and inert. It should be appreciated that n-heneicosane is chemically and electrically inert, so n-heneicosane does not affect any electronic components with which it comes in contact in either its solid or liquid form. However, in other embodiments, heat absorption medium 122 may not be in direct contact with many electronic components until after the heat absorption medium undergoes a state change, such as a phase change from a solid to a liquid. For example, one or more solid pieces of heat absorption material 122 may be placed within housing 102 in contact with power source 106. Such heat absorption medium 122 may not contact, for example, electronic assembly 108 until the heat absorption medium changes to a liquid phase.

In other embodiments, heat absorption medium 122 may not be in direct contact with electronic components either before or after the heat absorption medium undergoes a state change. For example, the heat absorption medium may be contained in compartments, containers, flexible pouches, capsules, etc. within housing 102 so that the heat absorption medium does not contact the electronic components. Alternatively, electronic assembly 108 is covered or shielded with a non-conductive coating prior to the insertion of heat absorption medium 122.

It is therefore a particular advantage of the invention that an implant 100 is provided having a housing 102, containing short circuit protection, which is of no greater than, or only slightly larger than a conventional implant. This is important because it is desirable to remove a minimal amount of tissue to implant the device 100. In addition, the complexity of the implant is not increased. For example, if a fuse is inserted in series with the power source an extra component is added to implant 100 which reduces its reliability. Due to the fact that heat absorption medium 122 is inert and does not encompass any moving parts, the complexity of the implant is not increased.

In some embodiments of the present invention, a heat sink, such as a metallic conductor is included in housing 102 to spread and dissipate heat. For example, in one embodiment, a heat sink is used to channel heat generated by power source 106 to a region in housing 102 in which a significant volume of heat absorption medium 122 is located. It should be appreciated that a heat sink may significantly increase the size of the housing which may be contrary to the desire to make certain medical implants as small as possible.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An implantable medical device comprising:
   a biocompatible housing comprising at least one fluidically sealing and thermally conductive divider integrally formed therein, said divider configured to divide the inside of said housing into two or more substantially fluidically sealed and thermally conductive compartments;
   an electronic assembly for processing sound into stimulation signals mounted in said housing;
   a power source mounted in a first of said fluidically sealed and thermally conductive compartments; and
   a heat absorption medium, sealed within a second of said fluidically sealed and thermally conductive compartments, thermally coupled to said power source, wherein said divider is configured to allow absorption of heat from said power source through said divider during a state change of said heat absorption medium.

2. The implantable medical device of claim 1, wherein said electronic assembly comprises a speech processor.

3. The implantable medical device of claim 1, wherein said heat absorption medium is configured to undergo state change at a temperature of approximately 34° Celsius or greater.

4. The implantable medical device of claim 1, wherein said maximum device temperature threshold is equal to or less than approximately 37° Celsius.

5. The implantable medical device of claim 1, wherein said heat absorption medium is configured to undergo said state change at a temperature between approximately 36° Celsius and approximately 43° Celsius.

6. The implantable medical device of claim 1, wherein said heat absorption medium is configured to undergo said state change at a temperature between approximately 39° Celsius and approximately 41° Celsius.

7. The implantable medical device of claim 1, wherein said heat absorption medium is configured to absorb at least 480 Joules of energy during said state change.

8. The implantable medical device of claim 1, wherein said heat absorption medium is configured to absorb at least 470 Joules of energy during said state change.

9. The implantable medical device of claim 1, wherein a state change temperature for said heat absorption medium is approximately equal to said maximum device threshold temperature.

10. The implantable medical device of claim 1, wherein said heat absorption medium comprises n-heneicosane.

11. The implantable medical device of claim 1, wherein said heat absorption medium is electrically non-conductive.

12. The implantable medical device of claim 1, wherein said power source comprises at least two batteries.

13. The implantable medical device of claim 1, wherein said implantable medical device is a tissue stimulating device.

14. The implantable medical device of claim 13, wherein said implantable medical device is a prosthetic hearing device.

15. The implantable medical device of claim 14, wherein said prosthetic hearing device is configured to be totally implantable.

16. The implantable medical device of claim 1, wherein said housing is hermetically sealed.

17. The implantable medical device of claim 1, wherein said device is adapted to be at least partially implanted in a recipient.

18. The implantable medical device of claim 1, wherein said device is adapted to be entirely implanted in a recipient.

19. The implantable medical device of claim 1, wherein said power source comprises a rechargeable battery.

20. A device comprising:
a housing;
a heat generating electronic assembly for processing sound into stimulation signals contained at least partially disposed within said housing;
a heat absorption capsule disposed within said housing, wherein the exterior of said heat absorption capsule is constructed of a fluidically sealing and thermally conductive capsule exterior material; and
a heat absorption medium sealed entirely within said capsule, wherein said heat absorption medium is separated from said electronic assembly by said fluidically sealing and thermally conductive capsule exterior material, and further wherein said heat absorption medium is configured to absorb heat from a power source through said fluidically sealing and thermally conductive capsule exterior to undergo a state change.

21. The device of claim 20, wherein said device further comprises:
a power source mounted in said housing.

22. The device of claim 21, wherein said power source comprises at least two batteries.

23. The device of claim 20, wherein said device is a medical implant.

24. The device of claim 23, wherein said medical implant is a tissue stimulating device.

25. The device of claim 24, wherein said medical implant is a prosthetic hearing device.

26. The device of claim 25, wherein said prosthetic hearing device is configured to be totally implantable.

27. The device of claim 20, wherein said heat absorption medium is configured to undergo a state change at a temperature of between approximately 36° and 43° Celsius.

28. The device of claim 20, wherein said heat absorption medium is configured to undergo a state change at a temperature of between approximately 39° and 41° Celsius.

29. The device of claim 20, wherein said heat absorption medium is configured to absorb at least 480 Joules before the temperature of said housing can reach said state change temperature.

30. The device of claim 20, wherein said heat absorption medium is configured to absorb at least 470 Joules before the temperature of said housing can reach said state change temperature.

31. The device of claim 20, wherein said heat absorption medium is electrically non-conductive and chemically inert.

32. The device of claim 20, wherein said heat absorption medium comprises n-heneicosane.

33. The device of claim 20, wherein said housing is biocompatible.

34. The device of claim 20, wherein said housing is a hermetically sealed titanium housing.

35. The device of claim 20, wherein said device is configured to be a totally implantable medical implant.

36. The device of claim 20, wherein said device is adapted to be at least partially implanted in an individual.

37. The device of claim 20, wherein said device is adapted to be entirely implanted in a recipient.

38. The implantable medical device of claim 1, wherein said biocompatible housing is configured so that said thermally conductive compartment is in direct contact with an exterior surface of said power source.

39. The implantable medical device of claim 1, wherein said biocompatible housing further comprises:
a conductor configured to thermally conductively couple said power source to said thermally conductive compartment.

40. The implantable medical device of claim 20, wherein said biocompatible housing is configured so that said thermally conductive capsule exterior of said heat absorption capsule is in direct contact with an exterior surface of said heat generating electronic assembly.

41. The implantable medical device of claim 20, wherein said biocompatible housing further comprises:
a conductor configured to thermally conductively couple said heat generating electronic assembly to said thermally conductive capsule exterior of said heat absorption capsule.

42. The implantable medical device of claim 1, wherein said state change is from a substantially solid state to a substantially liquid state.

43. The implantable medical device of claim 20, wherein said state change is from a substantially solid state to a substantially liquid state.

44. The implantable medical device of claim 1, wherein said heat absorption medium is configured to undergo said state change to prevent said electronic assembly from exceeding a maximum device temperature threshold.

45. The implantable medical device of claim 20, wherein said heat absorption medium is configured to undergo said state change to prevent said electronic assembly from exceeding a maximum device temperature threshold.

* * * * *